(12) United States Patent
Deo et al.

(10) Patent No.: US 9,107,538 B2
(45) Date of Patent: Aug. 18, 2015

(54) COLD PLASMA SANITATION FOR A DISPENSING MACHINE

(71) Applicant: PepsiCo., Inc., Purchase, NY (US)

(72) Inventors: Indrani Deo, Ossing, NY (US); Georgy Martsinovskiy, St. Petersburg (RU); Mikhail Verbitsky, Stoughton, MA (US); Dmitry Falkov, St. Petersburg (RU)

(73) Assignee: PepsiCo, Inc., Purchase, NY (US)

( * ) Notice: Subject to any disclaimer, the term of this patent is extended or adjusted under 35 U.S.C. 154(b) by 308 days.

(21) Appl. No.: 13/664,883

(22) Filed: Oct. 31, 2012

(65) Prior Publication Data

US 2013/0104742 A1    May 2, 2013

Related U.S. Application Data

(60) Provisional application No. 61/554,329, filed on Nov. 1, 2011.

(51) Int. Cl.
  *B67D 1/07*  (2006.01)
  *A47J 31/60* (2006.01)
  *B67D 3/00*  (2006.01)
  (Continued)

(52) U.S. Cl.
  CPC .............. *A47J 31/60* (2013.01); *B67D 1/0022* (2013.01); *B67D 1/07* (2013.01); *B67D 3/0058* (2013.01); *A61L 2/183* (2013.01); *B67D 2001/075* (2013.01); *B67D 2210/00023* (2013.01)

(58) Field of Classification Search
  CPC ........................... B67D 2001/075; B67D 1/07
  USPC .......... 99/286, 290; 222/148; 134/99.2, 100.1; 422/906, 255, 292
  See application file for complete search history.

(56) References Cited

U.S. PATENT DOCUMENTS

| 4,322,291 A | 3/1982 | Ho |
| 4,757,921 A | 7/1988 | Snowball |

(Continued)

FOREIGN PATENT DOCUMENTS

| GB | 2462278 A | 2/2010 |
| JP | 2001269637 A | 10/2001 |

(Continued)

OTHER PUBLICATIONS

International Search Report and Written Opinion in corresponding PCT application PCT/US2012/062790, mailed Feb. 6, 2013, pp. 1-18.

*Primary Examiner* — Reginald L Alexander
(74) *Attorney, Agent, or Firm* — Banner & Witcoff, Ltd.

(57) ABSTRACT

An apparatus comprises a dispensing system and a sanitizing system. The apparatus has a dispensing mode and sanitizing mode. The dispensing system may comprise a first valve and at least one component, the at least one component having an inner surface. The first valve is opened to send a free-flowing material to the at least one component when the apparatus is in the dispensing mode. The first valve is closed when the apparatus is in the sanitizing mode. The sanitizing system comprises a processing unit having a discharge cell configured to initiate a cold plasma discharge in an air flow. A tank may be configured to receive the air flow from the discharge cell of the processing unit and expose water in the tank to the air flow for a time sufficient to provide dissolution of ozone from the air flow into the water and form ozone-containing water.

16 Claims, 4 Drawing Sheets

(51) Int. Cl.
*B67D 1/00* (2006.01)
*A61L 2/18* (2006.01)

(56) References Cited

U.S. PATENT DOCUMENTS

| | | | |
|---|---|---|---|
| 4,867,052 A | 9/1989 | Cipelletti | |
| 4,969,991 A | 11/1990 | Valadez | |
| 5,064,097 A | 11/1991 | Brog et al. | |
| 5,316,673 A | 5/1994 | Kohlmann et al. | |
| 5,339,874 A | 8/1994 | Cragun | |
| 5,450,882 A | 9/1995 | Cragun | |
| 5,484,538 A | 1/1996 | Woodward | |
| 5,636,763 A * | 6/1997 | Furness | 222/54 |
| 6,077,427 A | 6/2000 | Burrows | |
| 6,216,918 B1 | 4/2001 | Saveliev et al. | |
| 6,334,328 B1 | 1/2002 | Brill | |
| 6,354,341 B1 | 3/2002 | Saveliev et al. | |
| 6,382,467 B2 | 5/2002 | Saveliev et al. | |
| 6,449,970 B1 | 9/2002 | Gagliano | |
| 6,483,119 B1 | 11/2002 | Baus | |
| 6,695,168 B2 | 2/2004 | Pinedjian et al. | |
| 8,459,178 B2 * | 6/2013 | Miller | 99/289 R |
| 2001/0010318 A1 | 8/2001 | Saveliev et al. | |
| 2002/0083842 A1 | 7/2002 | Kown | |
| 2005/0172833 A1 * | 8/2005 | Ioannone et al. | 99/453 |
| 2005/0247614 A1 | 11/2005 | Wiemer et al. | |
| 2006/0175352 A1 | 8/2006 | Emmendorfer et al. | |
| 2007/0137726 A1 | 6/2007 | Yan | |
| 2007/0272620 A1 | 11/2007 | Chaney | |
| 2008/0142037 A1 | 6/2008 | Dempski et al. | |
| 2008/0277272 A1 * | 11/2008 | Pierce et al. | 204/164 |
| 2009/0183754 A1 * | 7/2009 | Vetterli et al. | 134/18 |
| 2009/0185953 A1 | 7/2009 | Hallam et al. | |
| 2010/0101929 A1 | 4/2010 | Kamen et al. | |
| 2010/0176147 A1 | 7/2010 | Segers | |
| 2010/0247374 A1 | 9/2010 | Pellet | |
| 2011/0006085 A1 * | 1/2011 | Davis et al. | 222/190 |

FOREIGN PATENT DOCUMENTS

| | | |
|---|---|---|
| WO | 02100766 A1 | 12/2002 |
| WO | 02102706 A1 | 12/2002 |

* cited by examiner

COLD PLASMA SANITATION FOR A DISPENSING MACHINE

CROSS REFERENCE TO RELATED APPLICATIONS

This application is a non-provisional of and claims priority to pending provisional U.S. Application No. 61/554,329, filed Nov. 1, 2011, and entitled "Cold Plasma Sanitation for Dispensing Machine," the entire disclosure of which is hereby incorporated by reference in its entirety and for all purposes.

FIELD OF THE INVENTION

This disclosure relates generally to a cold plasma sanitization of dispensing systems, e.g., free-flowing food dispensing systems, such as beverage dispensers used in cafeterias, restaurants (including fast food restaurants), theatres, convenience stores, gas stations, and other entertainment and/or food service venues.

BACKGROUND

Dispensing systems, e.g., free-flowing food dispensing systems, including beverage dispensers, periodically need to be sanitized. Traditional methods of sanitizing dispensing systems utilize disinfecting liquids, which typically include antimicrobial agents, liquid detergents, and surfactants. A disadvantage of conventional systems is related to the need for reloading or recharging the disinfecting and cleaning liquids to a sanitizing system. The reloading or recharging of disinfecting and cleaning liquids complicates system maintenance and hinders automation of sanitizing processes.

Therefore, there is a need for new disinfection and sanitization apparatus and methods that would eliminate the need for reloading of disinfecting and cleaning liquids as in existing apparatuses and methods. Further, eliminating the need for reloading of disinfecting and cleaning liquids, and would also enable easier automation of sanitization of beverage dispensing systems.

SUMMARY

An aspect of the present disclosure includes an apparatus comprising a dispensing system in combination with a sanitizing system. The combination has a dispensing mode and sanitizing mode. The dispensing system comprises a first valve and at least one component, the at least one component comprising an inner surface. In an embodiment, the first valve has an open position to send a free-flowing material to the at least one component when the combination is in the dispensing mode. The first valve has a closed position when the combination is in the sanitizing mode. The sanitizing system comprises a processing unit. The processing unit comprises a discharge cell, a high voltage driver, and a tank. The high voltage driver is configured to control the discharge cell. The discharge cell is configured to initiate a cold plasma discharge in an air flow. The tank is configured to receive the air flow from the discharge cell and expose water in the tank to the air flow for a time sufficient to provide dissolution of ozone from the air flow into the water and form ozone-containing water. The sanitizing system further comprises a second valve. The second valve has an open position to send the ozone-containing water from the tank to the at least one component when the combination is the sanitizing mode. The second valve has a closed position when the combination is the dispensing mode.

The above and other aspects, features and advantages of the present disclosure will be apparent from the following detailed description of the illustrated embodiments thereof which are to be read in connection with the accompanying drawings.

DETAILED DESCRIPTION OF EMBODIMENTS

Figure 1:
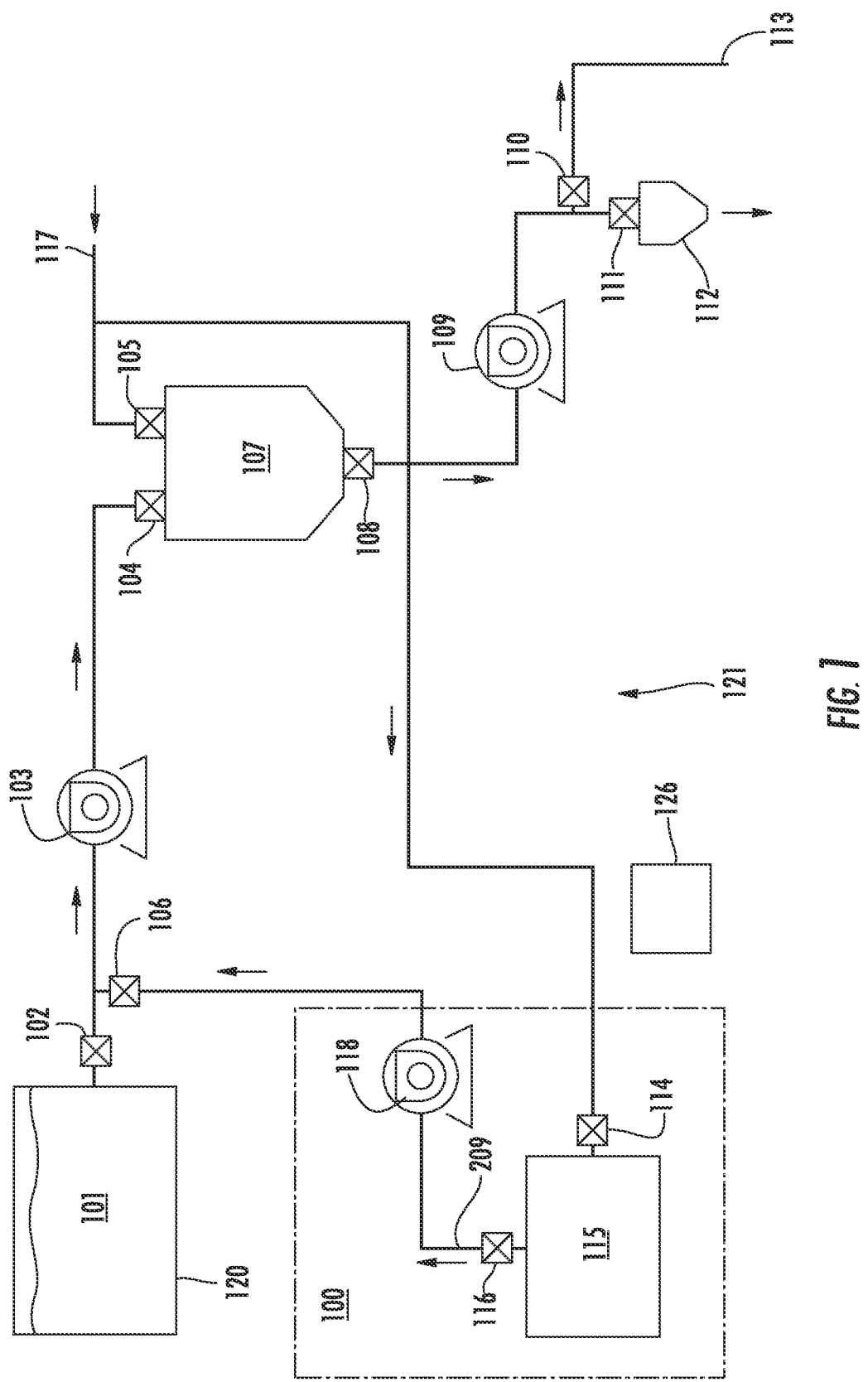
FIG. 1 shows a system in accordance with various aspects of the disclosure.

The present disclosure relates to sanitizing and/or cleaning systems, and more particularly to systems that generate a working liquid having cleaning and/or sanitizing properties.

An aspect of the present disclosure is to provide an automated sanitizing system that modifies properties of water in such way that water acquires disinfecting and/or cleaning properties. As a result, the sanitizing system does not require any consumable disinfecting and/or cleaning materials.

An aspect of the present disclosure is generating an ozone-water solution or ozone-containing liquid that may have antimicrobial effectiveness, and using that ozone-containing liquid to disinfect or sanitize an inner surface(s) of components of a dispensing system. Such solutions may be obtained by mixing of ozone with water, for example by bubbling. An aspect of the present disclosure comprises using an ozone generator. The ozone generator may be based on action of corona discharge or by UV radiation on air or pure oxygen. An aspect of the present disclosure includes drying of air to increase oxygen concentration.

An aspect of the present disclosure comprises use of a regular water supply in combination with ozone to eliminate reloading of disinfecting and cleaning liquids. An aspect of the disclosure comprises use of a regular water supply in combination with ozone to enable easier automation of sanitization of dispensing systems. An aspect of the disclosure provides effective integration of a unit for production of ozone-water solution with a dispensing system to provide reliable and automated sanitization.

In accordance with the present disclosure, a sanitizing method is provided that is based on modification of water in a manner that the water acquires antimicrobial and cleaning properties. According to the present disclosure, water properties may be modified by saturation of water with ozone and other ions and chemical radicals produced by a cold plasma generator. The ozone-saturated water may be pumped through a dispensing system in order to sanitize and clean the inner surface(s) of pipes, chambers, reservoirs, pumps, valves and other components of the dispensing system. Use of regular a water supply may eliminate the need for reloading of disinfecting and cleaning liquids, thus enabling easier automation of sanitization of free-flowing or liquid dispensing systems. Liquid dispensing systems may comprise free-flowing food dispensing systems, e.g. beverage dispensing systems.

In an embodiment of the disclosure, a sanitization method comprises (1) providing air flow through a discharge chamber, the discharge chamber in proximity to discharge electrodes, (2) initiating a cold plasma discharge into the air flow, (3) after initiating the cold plasma discharge into the air flow, exposing a liquid to the air flow for time sufficient to provide dissolution of ozone and other ions and chemical radicals from the air flow into the liquid, thereby producing ozonated liquid, and (4) sending the liquid through a beverage dispensing system. In an embodiment, the liquid comprises water. In an embodiment, the liquid is water.

In an aspect of the disclosure, pumping of ozonated liquid through the beverage dispensing system can be arranged in such way that the liquid, e.g., water, circulates though the beverage dispensing system and returns to the sanitizing system. By re-circulating the ozonated liquid, the liquid may again exposed to the air flow to replenish ozone, ions and chemical radicals in the liquid, and the ozonated liquid may be sent again through the dispensing system. Alternatively, a single pass of the ozonated liquid through the dispensing system can be arranged. After the sanitizing procedure is completed, the liquid may be disposed into a drain or further processed as may be desired.

In an aspect of the disclosure, a liquid, such as water, is treated in such a way that the liquid acquires antimicrobial and cleaning properties. In an embodiment, water properties may be modified by saturation of water with ozone and other ions and chemical radicals produced by a cold plasma generator. The ozone saturated water may be pumped through a dispensing system to sanitize and clean the inner surface(s) of pipes, chambers, reservoirs, pumps, valves and other components of the dispensing system. Use of regular water supply can eliminate the need for reloading of disinfecting and cleaning liquids, thus enabling easier automation of sanitizing process.

The sanitizing method may include providing air flow through a discharge chamber in proximity to discharge electrodes, initiating of a cold plasma discharge into the air flow, putting the air flow through water, exposing the water to the air flow to provide dissolution of ozone and other ions and chemical radicals from the air flow into the water, and pumping the water through a dispensing system.

In an embodiment, ozone-containing water may be circulated inside a dispensing system for a sufficient time to provide sanitization of the dispensing system so that free-flowing material, such as free-flowing food (e.g., a beverage) can be dispensed from the dispensing system without being contaminated by components of the dispensing system, or other materials within components of the dispensing system.

In accordance with the present disclosure, an ozonated liquid, e.g., ozone-containing water, may be generated and circulated inside components of a beverage dispensing system. In an embodiment, ozone-containing water may be circulated inside the beverage dispensing system for a sufficient time to provide sanitization of the beverage dispensing system so that a beverage can be dispensed from the beverage dispensing system without being contaminated by the beverage dispensing system. In accordance with the present disclosure, those skilled in the art will recognize that an ozone-water solution or ozone-containing water may be circulated inside the beverage dispensing system for not longer than about 30 minutes before it is disposed to a drain or is returned to a processing unit for replenishment of ozone. By maintaining circulation of the ozone-containing water to not longer than 30 minutes may provide greater antimicrobial efficacy of the ozone-containing water than circulating the ozone-containing water for longer than 30 minutes.

After the ozone-water solution or ozone-containing water is circulated inside the beverage dispensing system for sufficient time for the beverage dispensing system to be sanitized, the ozone-containing water may be either returned to an ozone-water mixing unit or tank, or disposed to a drain. Disposing the ozone-containing water to the drain after one pass, and generating a new ozone-containing water to circulate through the beverage dispensing system may provide better antimicrobial efficacy than simply recirculating the older ozone-water solution through the beverage dispensing system.

An embodiment of a sanitizing system 100 in accordance with the present disclosure is shown in FIG. 1. As shown in FIG. 1, sanitizing system 100 may be integrated with a beverage dispensing system 121. The beverage dispensing apparatus or system 121 may be used to dispense a concentrated beverage. The beverage dispensing system 121 may comprise a container 120, with concentrate 101, mixer 107, pumps 103 and 109, dispensing nozzle 112, and valves 102, 104, 105, 108, 110, 111. The sanitizing system 100 may include a processing unit 115, an input valve 114, an output valve 116, and a pump 118.

When beverage dispensing system 121 is in dispensing mode, valves 106, 110 and 114 may be closed. In the dispensing mode, pump 103 may move concentrate 101 from container 120 into mixer 107, and valves 102 and 104 may be open. Water may be delivered to the mixer 107 from the water supply 117 and through valve 105. Water supply 117 may be any conventional drinking water supply, e.g., municipal tap water. After mixing in the mixer 107, the mixture of concentrate 101 and water may be pumped to nozzle 112 by pump 109, and further into a cup or other container (not shown) placed under nozzle 112.

In the sanitizing mode, valve 102 may be closed so that concentrate 101 does not flow from container 120 to pump 103. In the sanitizing mode, valve 114 may be open or opened and water from water supply 117 may be directed into processing unit 115. Pump 118 may direct the water, which may be processed by cold plasma in processing unit 115, into beverage dispensing system 121 through valve 106, which may be open in the sanitizing mode. In an embodiment, processed water from processing unit 115 may be sent from valve 106 through pump 103, mixer 107 and pump 109 and into drain 113. In an embodiment, valve 111 may be closed and valve 110 may be open.

Figure 2:
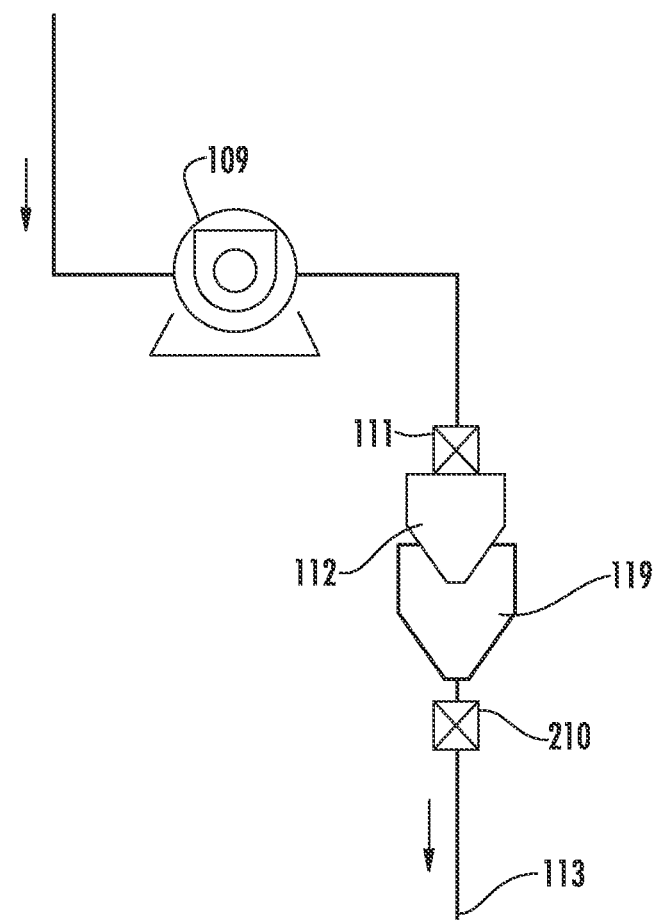
FIG. 2 shows a portion of a system in accordance with various aspects of the disclosure.

Alternatively, disinfecting or sanitizing water can be directed through the nozzle 112. In this case, a receiving plate 119 may be connected to drain 113, as shown in FIG. 2. Thus, disinfecting or sanitizing water may be directed through nozzle 112 to receiving plate 119, and through valve 210, as shown in FIG. 2.

Figure 3:
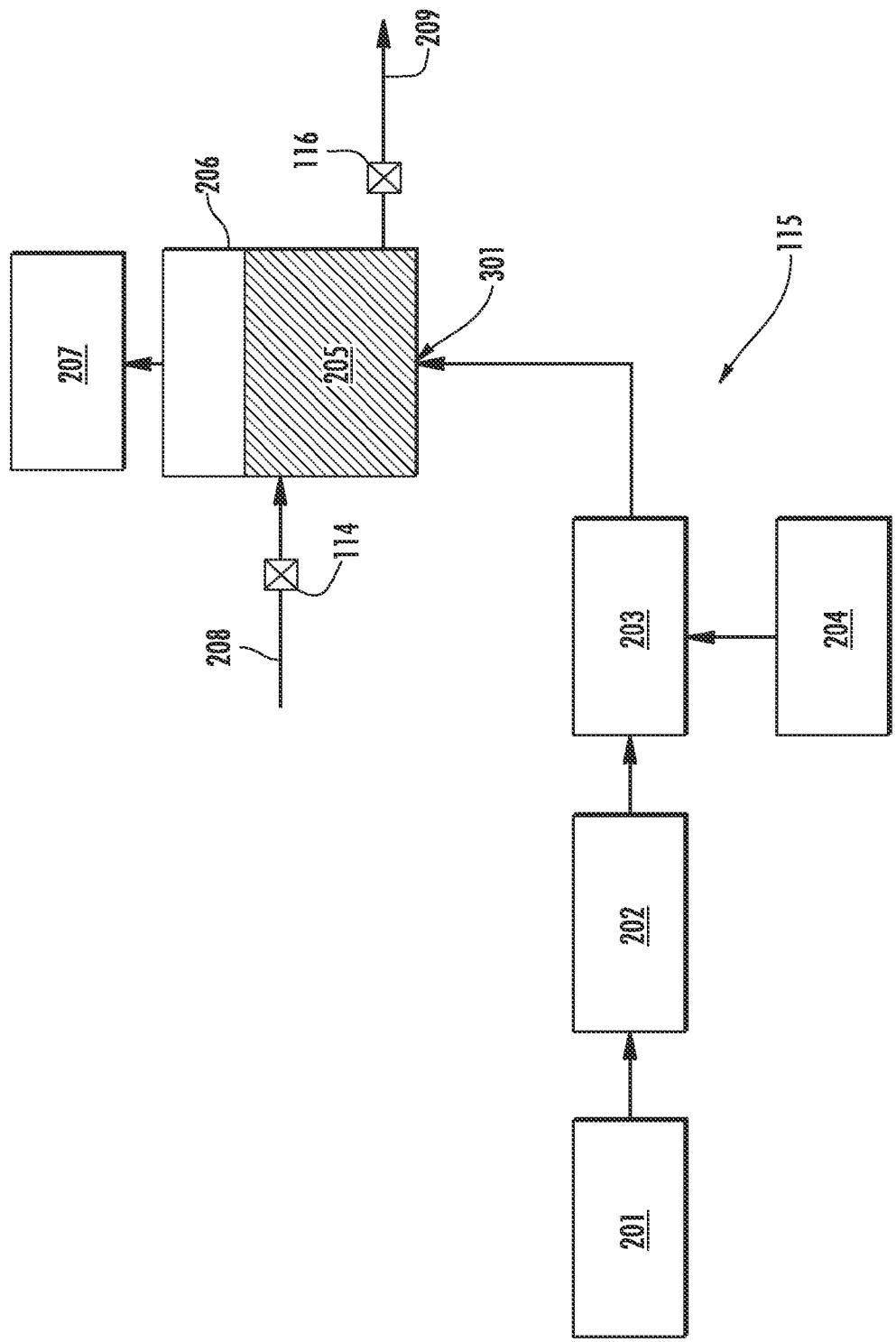
FIG. 3 shows a processing unit in accordance with various aspects of the present disclosure.

An embodiment of the processing unit 115 is shown in FIG. 3. The processing unit 115 may comprise an air dryer 201, a compressor 202, a discharge cell 203, a high voltage driver 204, a water tank 206, and a catalytic convertor 207, which converts ozone into diatomic oxygen.

In an aspect of the disclosure, air passes through the air dryer 201 and then passes through compressor 202 and then enters discharge cell 203. Drying the air before it enters discharge cell 203 increases efficiency of the air ionization in the discharge. The discharge cell 203 may be controlled by high voltage driver 204, which may provide signals to discharge cell 203 to start and maintain cold plasma discharge. In the discharge cell 203, the air may be subjected to discharge from the discharge electrodes (not shown) of the discharge cell 203. Upon being subjected to this discharge, the air may become ionized and contain a high concentration of ozone, ions and chemical radicals. This air may be sent to water tank 206, where ozone and other processed air components may be dissolved into water 205 held within water tank 206. In an embodiment, air treated in discharge cell 203 may be bubbled into the water 205 through bottom 301 of water tank 206. As a result, water 205 may obtain antimicrobial and cleaning properties. The portion of the air that is not absorbed by water may be further directed into a catalytic converter 207, e.g. a thermo-catalytic converter, where remaining ozone may be decomposed into diatomic oxygen to provide operational safety.

The water tank 206 may be filled with water from inlet 208, which may flow through valve 114. Inlet 208 may be supplied with water from water supply 117. The processed water 205 may be moved from tank 206 through outlet 209. The processed water may flow from outlet 209 to pump 118, as shown in FIG. 1.

In an embodiment, a controller 126 may control operation of the sanitizing system 100, including components thereof. In an embodiment, controller 126 may control beverage dispensing system 121, including components thereof.

Those of ordinary skill in the art will recognize that in accordance with the present disclosure, in an embodiment, air flow rates, discharge power, and water flow may be coordinated in an amount and manner that desirable ozone concentration in water is achieved.

Figure 4:
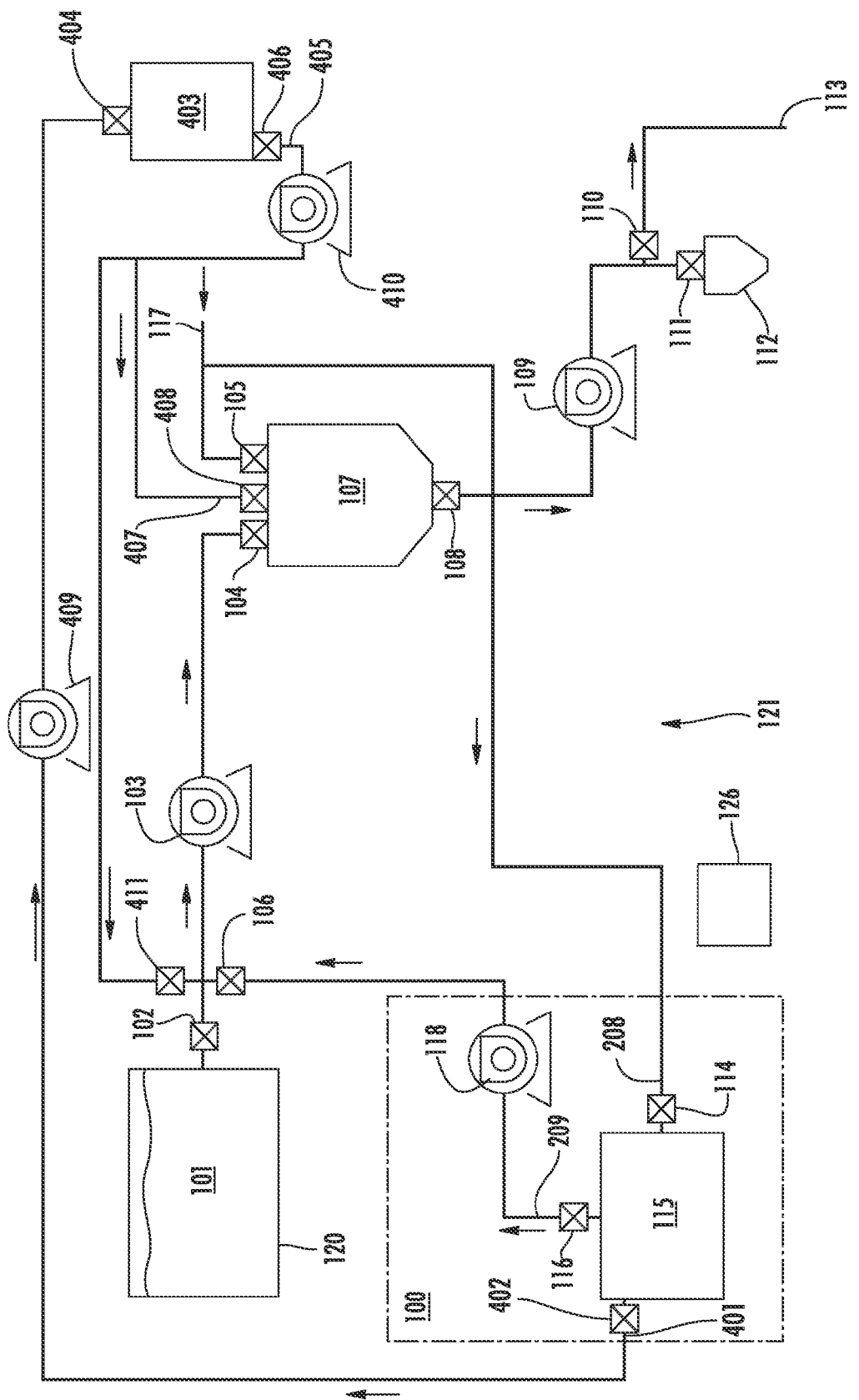
FIG. 4 shows a system in accordance with various aspects of the disclosure.

In an embodiment, processing unit 115 may be utilized to clean water from water supply 117. In an embodiment, processing unit 115 can be utilized not only for ozone-water solution production to sanitize the system, but also for cleaning water from the water supply 117. As shown in FIG. 4, in such an embodiment, processing unit 115 may have two outputs or outlets—one outlet 209 containing ozone-water solution to sanitize the beverage dispensing system 121, and a second outlet 401 containing water, where ozone and other ions and chemical radicals produced by a cold plasma generator may be removed by apparatus 403, thereby resulting in cleaner water than water from water supply 117. As shown in FIG. 4, water treated by processing unit 115 may exit unit 115 through valve 402 and second outlet 401. The water may be sent through valve 404 and into apparatus 403. In apparatus 403, ozone and other ions and chemical radicals in the water may be removed, and water may exit apparatus 403 through valve 406 and outlet 405. As shown in FIG. 4, water from apparatus 403 may be used as a water supply 407 to mixer 107. Water supply 407 may be used in combination with water supply 117 to supply water to mixer 107, or may be used as an alternative to water supply 117. Water supply 407 may flow through valve 408 before flowing into mixer 407. A pump 409 may be used to send water from processing unit 115 to apparatus 403. A pump 410 may be used to pump water from apparatus 403 to mixer 107. Thus, water treated in apparatus 403 can be used as a water supply to mixer 107, and be combined with concentrate 101 when desired to prepare a beverage using water that has been cleaned using the combination of processing unit 115 and apparatus 403. Those of skill in the art will recognize that in accordance with the present disclosure, any suitable apparatus 403 may be used to remove from water ozone and other ions and chemical radicals produced by a cold plasma generator of processing unit 115, thereby resulting in an ozone-free water.

Those of skill in the art will recognize that in accordance with the present disclosure, any suitable apparatus 403 may be used to remove from water the ozone and other ions and chemical radicals produced by the cold plasma generator of processing unit 115. Thus, apparatus 403 may comprise, for example, an ultraviolet (UV) radiation emitter, which subjects ozonated water to UV radiation to break one of the oxygen-oxygen bonds in each ozone molecule. The resulting free oxygen atom may then combine with another oxygen atom to for diatomic oxygen. In an embodiment, ozonated water may be subjected to UV radiation having a wavelength of about 254 nanometers (nm), which is a wavelength at which ozone is sensitive. In an embodiment, UV radiation may be emitted by UV lamps that may have a quartz shield configured to block light with a wavelength of about 185 nm, as this radiation has a potential for creating ozone.

Apparatus 403 may be configured to subject ozonated water to hydrogen peroxide to remove ozone from the water. This procedure may also be called ozone quenching.

Apparatus 403 may comprise activated carbon to absorb ozone from the water. Using activated carbon may not only absorb and thus remove ozone from the water, but may also remove other ions and chemical radicals produced by the cold plasma generator of processing unit 115.

Automation of a sanitization process in accordance with at least one aspect of the present disclosure can be done according to the following steps.

a. The sanitization process may be started by pre-set timer or by a received input, for example, by receiving a "start signal."

b. A dispensing system 121 may enter into a sanitizing mode wherein valves 102 and 111 may be closed, and valve 110 may be opened.

c. Valve 114 may be opened to fill processing tank 206 of processing unit 115 from inlet 208, which in turn may be supplied with water from water supply 117. When the tank 206 is filled to a desired level, valve 114 may be closed.

d. The air flow through the discharge chamber or cell 203 may be started and discharge arc may be initiated.

e. The water treated in tank 206 may be bubbled with treated or activated air from discharge chamber 203 for a time sufficient to achieve a desired concentration of ozone in water for a given temperature of the solution. In an embodiment, the desired concentration is the maximum concentration of ozone in water for a given temperature of the solution. Then, valve 116 may be opened and pumps 118, 103, and 109 may move the treated or activated water through dispensing system 121.

f. Steps a-e may be are repeated more than one time to achieve desirable disinfection and cleaning efficacy, i.e. commercial sanitization.

g. After step f is completed, if desired, water can be further treated in apparatus 403 as previously discussed, and the water treated in apparatus 403 may be sent to a location in the beverage dispensing system 121 to purge any ozonated water remaining in beverage dispensing system 121. Thus, water treated in sanitizing system 100 can be sent to apparatus 403 further treatment as discussed above, and then can be sent from apparatus 403, e.g., through valve 411, which may be positioned upstream of pump 103. The water treated in apparatus 403 can then flow through valve 411 and downstream components, e.g., pump 103, valve 104, mixer 107, valve 108, pump 109, valve 111, and nozzle 112. Alternatively, although not shown in FIG. 4, water treated in apparatus 403 can be sent to valve 106, and then through downstream components, e.g., pump 103, valve 104, mixer 107, valve 108, pump 109, valve 111, and nozzle 112.

An aspect of the present disclosure includes an apparatus comprising a dispensing system in combination with a sanitizing system. The combination may have a dispensing mode and sanitizing mode. The dispensing system may comprise a first valve and at least one component, the at least one component comprising an inner surface. In an embodiment, the first valve may be open to send a free-flowing material to the at least one component when the combination is in the dispensing mode. The first valve may be closed when the combination is in the sanitizing mode. The sanitizing system may also include a processing unit. The processing unit may comprise a discharge cell, a high voltage driver, and a tank. The high voltage driver may be configured to control the discharge cell. The discharge cell may be configured to initiate a cold plasma discharge in an air flow. The tank may be configured to receive the air flow from the discharge cell and expose water in the tank to the air flow for a time sufficient to provide dissolution of ozone from the air flow into the water and form ozone-containing water. The sanitizing system may further comprise a second valve. The second valve may be open to send the ozone-containing water from the tank to the at least one component when the combination is the sanitizing mode. The second valve may be closed when the combination is the dispensing mode.

In a further aspect of the disclosure, the at least one component may be selected from the group consisting of a pipe, a mixer, a chamber, a reservoir, a pump, a third valve, and a nozzle.

In a further aspect of the disclosure, when the air flow is exposed to water in the tank, the ozone-containing water formed in the tank further comprises ions and radicals.

In a further aspect of the disclosure, the apparatus may comprise at least one pump. The pump may be configured to send the ozone-containing water across the interior surface of the component when the combination is in the sanitizing mode.

In a further aspect of the disclosure, the apparatus may comprise piping. The piping may be configured to send the ozone-containing water to the tank of the sanitizing system after the ozone-containing water has made at least one pass across the interior surface of the component.

In a further aspect of the disclosure, the apparatus may comprise a drain. The drain may be configured to receive the ozone-containing water after the ozone-containing water has made at least one pass across the interior surface of the component.

In a further aspect of the disclosure, the apparatus may be configured to send the ozone-containing water across the interior surface of the component until the interior surface of the component has been sanitized.

In a further aspect of the disclosure, the discharge cell may comprise a discharge chamber and discharge electrodes.

In a further aspect of the disclosure, the discharge cell may be configured to provide a discharge to the air flow, the discharge selected from the group consisting of corona discharge and UV radiation.

In a further aspect of the disclosure, the apparatus may comprise an air dryer. The air dryer may be configured to dry the air flow before the discharge cell initiates a cold plasma discharge in the air flow.

In a further aspect of the disclosure, the apparatus may comprise a compressor. The compressor may be configured to send the air flow through the air dryer.

In a further aspect of the disclosure, the free-flowing material may be a beverage concentrate.

In a further aspect of the disclosure, the apparatus comprises a catalytic converter. The catalytic converter may be configured receive remaining ozone in the air that is not absorbed by water in the tank and decompose the remaining ozone into diatomic oxygen.

In a further aspect of the disclosure, the catalytic converter may be a thermo-catalytic converter.

In a further aspect of the disclosure, the apparatus may comprise a device configured to receive ozone-containing water from the sanitizing system and remove the ozone from the ozone-containing water to generate ozone-free water. The apparatus may be configured to supply the ozone-free water across the interior surface of the at least one component to purge any ozone-containing water from the dispensing system. The dispensing system may be a beverage dispensing system.

In a further aspect of the disclosure, the apparatus may comprise a device configured to receive ozone-containing water from the sanitizing system and remove the ozone from the ozone-containing water to generate ozone-free water. The apparatus may be configured to supply the ozone-free water to a mixer. The mixer may be configured to mix a beverage concentrate with the ozone-free water when the combination is in the dispensing mode.

In another aspect of the present disclosure, an apparatus is provided, the apparatus comprising a beverage dispensing system in combination with a sanitizing system, the combination having a dispensing mode and sanitizing mode. The beverage dispensing system may comprise a first valve and a mixer. The mixer may have an inner surface. The mixer may be configured to mix a beverage concentrate with water when the combination is in the dispensing mode. The first valve may be open to send the beverage concentrate to the mixer when the combination is in the dispensing mode. The first valve may be closed when the combination is in the sanitizing mode. The sanitizing system may also comprise a processing unit. The processing unit may comprise a discharge cell, a high voltage driver, and a tank. The high voltage driver may be configured to control the discharge cell. The discharge cell may be configured to initiate a cold plasma discharge in an air flow. The tank may be configured to receive the air flow from the discharge cell and expose water in the tank to the air flow for a time sufficient to provide dissolution of ozone from the air flow into the water and form ozone-containing water. The sanitizing system may further comprise a second valve. The second valve may be open to send the ozone-containing water from the tank to the mixer when the combination is in the sanitizing mode. The second valve may be closed when the combination is in the dispensing mode.

In yet another aspect of the present disclosure a method for sanitizing interior surfaces of a dispensing system is provided. The method may comprise providing an air flow through a discharge chamber. The discharge chamber may be in proximity to discharge electrodes. The method may comprise initiating a cold plasma discharge in the air flow. After initiating the cold plasma discharge in the air flow, the method may further comprise exposing a liquid to the air flow for time sufficient to provide dissolution of ozone and other ions and chemical radicals from the air flow into the liquid. After dissolution of ozone and other ions and chemical radicals from the air flow into the liquid, the liquid may be sent through the dispensing system. The dispensing system may be a beverage dispensing system.

In a further aspect of the disclosure the liquid may be water. The method may comprise closing a first valve, the first valve at the outlet of a beverage concentrate supply. The method may comprise receiving an air flow in the discharge chamber. The method may comprise initiating in the discharge chamber a cold plasma discharge in the air flow. The method may comprise exposing the water in a water tank to the air flow from the discharge chamber for a time sufficient to provide dissolution of ozone from the air flow into the water and forming ozone-containing water. The method may comprise sending the ozone-containing water from the water tank to an interior surface of a component of the beverage dispensing system to sanitize the interior surface of the component.

In a further aspect of the disclosure, the method may comprise opening a second valve, the second valve located at the outlet of the water tank.

As will be recognized by those skilled in the art, the above described embodiments may be configured to be compatible with fountain system requirements, and can accommodate a wide variety of fountain offerings, including but not limited beverages known under any PepsiCo branded name, such as Pepsi-Cola®, and custom beverage offerings. The embodiments described herein offer speed of service at least and fast or faster than conventional systems. The embodiments described herein may be configured to be monitored, including monitored remotely, with respect to operation and supply levels. The embodiments described herein are economically viable and can be constructed with off-the-shelf components, which may be modified in accordance with the disclosures herein.

Those of skill in the art will recognize that in accordance with the disclosure any of the features and/or options in one embodiment or example can be combined with any of the features and/or options of another embodiment or example.

The disclosure herein has been described and illustrated with reference to the embodiments of the figures, but it should be understood that the features of the disclosure are susceptible to modification, alteration, changes or substitution without departing significantly from the spirit of the disclosure. For example, the dimensions, number, size and shape of the various components may be altered to fit specific applications. Accordingly, the specific embodiments illustrated and described herein are for illustrative purposes only and the disclosure is not limited except by the following claims and their equivalents.

We claim:

1. An apparatus comprising:
a dispensing system in combination with a sanitizing system, the combination having a dispensing mode and sanitizing mode,
the dispensing system comprising a first valve and at least one component, the at least one component having an interior surface, the first valve having an open position to send a free-flowing material to the at least one component when the combination is in the dispensing mode, the first valve having a closed position when the combination is in the sanitizing mode,
the sanitizing system comprising a processing unit,
the processing unit comprising a discharge cell, a high voltage driver, and a tank,
the high voltage driver configured to control the discharge cell,
the discharge cell configured to initiate a cold plasma discharge in an air flow,
the tank configured to receive the air flow from the discharge cell and expose water in the tank to the air flow for a time sufficient to provide dissolution of ozone from the air flow into the water and form ozone-containing water,
the sanitizing system further comprising a second valve, the second valve having an open position to send the ozone-containing water from the tank to the at least one component when the combination is the sanitizing mode, the second valve having a closed position when the combination is the dispensing mode,
the apparatus further comprising at least one pump, the pump configured to send the ozone-containing water across the interior surface of the component when the combination is in the sanitizing mode.

2. The apparatus of claim 1, wherein the at least one component is selected from the group consisting of a pipe, a mixer, a chamber, a reservoir, a pump, a third valve, and a nozzle.

3. The apparatus of claim 1, wherein when the air flow is exposed to water in the tank, the ozone-containing water formed in the tank further comprises ions and radicals.

4. The apparatus of claim 1, further comprising piping configured to send the ozone-containing water to the tank of the sanitizing system after the ozone-containing water has made at least one pass across the interior surface of the component.

5. The apparatus of claim 1, further comprising a drain, the drain configured to receive to the ozone-containing water after the ozone-containing water has made at least one pass across the interior surface of the component.

6. The apparatus of claim 1, the apparatus configured to send the ozone-containing water across the interior surface of the component until the interior surface of the component has been sanitized.

7. The apparatus of claim 1, wherein the discharge cell comprises a discharge chamber and discharge electrodes.

8. The apparatus of claim 1, wherein the discharge cell is configured to provide a discharge to the air flow, the discharge selected from the group consisting of corona discharge and UV radiation.

9. The apparatus of claim 1 further comprising an air dryer, the air dryer configured to dry the air flow before the discharge cell initiates a cold plasma discharge in the air flow.

10. The apparatus of claim 9 further comprising a compressor, the compressor configured to send the air flow through the air dryer.

11. The apparatus of claim 1, wherein the free-flowing material is a beverage concentrate.

12. The apparatus of claim 1 further comprising a catalytic converter, the catalytic converter configured receive remaining ozone in the air that is not absorbed by water in the tank and decompose the remaining ozone into diatomic oxygen.

13. The apparatus of claim 12, wherein the catalytic converter is a thermo-catalytic converter.

14. The apparatus of claim 1, further comprising a device configured to receive ozone-containing water from the sanitizing system and remove the ozone from the ozone-containing water to generate ozone-free water, the apparatus further configured to supply the ozone-free water across the interior surface of the component to purge any ozone-containing water from the dispensing system.

15. The apparatus of claim 1, further comprising a device configured to receive ozone-containing water from the sanitizing system and remove the ozone from the ozone-containing water to generate ozone-free water, the apparatus further configured to supply the ozone-free water to a mixer, the mixer configured to mix a beverage concentrate with the ozone-free water when the combination is in the dispensing mode.

16. An apparatus comprising:
a beverage dispensing system in combination with a sanitizing system, the combination having a dispensing mode and sanitizing mode,
the beverage dispensing system comprising a first valve and a mixer, the mixer having an inner surface, the mixer configured to mix a beverage concentrate with water when the combination is in the dispensing mode, the first valve having an open position to send a free-flowing material to the mixer when the combination is in the dispensing mode, the first valve having a closed position when the combination is in the sanitizing mode, the sanitizing system comprising a processing unit, the processing unit comprising a discharge cell, a high voltage driver, and a tank, the high voltage driver configured to control the discharge cell, the discharge cell configured to initiate a cold plasma discharge in an air flow, the tank configured to receive the air flow from the discharge cell and expose water in the tank to the air flow for a time sufficient to provide dissolution of ozone from the air flow into the water and form ozone-containing water, the sanitizing system further comprising a second valve, the second valve having an open position to send the ozone-containing water from the tank to the mixer when the combination is in the sanitizing mode, the second valve having a closed position when the combination is in the dispensing mode, the apparatus further comprising at least one pump, the pump configured to send the ozone-containing water across the interior surface of the component when the combination is in the sanitizing mode.

* * * * *